United States Patent
Lee et al.

(10) Patent No.: US 11,974,838 B2
(45) Date of Patent: May 7, 2024

(54) ELECTRONIC DEVICE FOR ACQUIRING BIOMETRICS USING PPG SENSOR, AND METHOD THEREFOR

(71) Applicant: Samsung Electronics Co., Ltd., Gyeonggi-do (KR)

(72) Inventors: Hansung Lee, Gyeonggi-do (KR); Hwan Shim, Gyeonggi-do (KR); Yongjin Lee, Gyeonggi-do (KR); Jooman Han, Gyeonggi-do (KR); Jongho Park, Gyeonggi-do (KR); Gahee Jung, Gyeonggi-do (KR); Seounghun Kim, Gyeonggi-do (KR); Jihwan Kim, Gyeonggi-do (KR); Choonghee Ahn, Gyeonggi-do (KR); Hyungjoon Lim, Gyeonggi-do (KR); Jiwoon Jung, Gyeonggi-do (KR); Jeongmin Park, Gyeonggi-do (KR)

(73) Assignee: Samsung Electronics Co., Ltd (KR)

(*) Notice: Subject to any disclaimer, the term of this patent is extended or adjusted under 35 U.S.C. 154(b) by 959 days.

(21) Appl. No.: 16/964,087

(22) PCT Filed: Jan. 9, 2019

(86) PCT No.: PCT/KR2019/000345
§ 371 (c)(1),
(2) Date: Jul. 22, 2020

(87) PCT Pub. No.: WO2019/151668
PCT Pub. Date: Aug. 8, 2019

(65) Prior Publication Data
US 2021/0030290 A1   Feb. 4, 2021

(30) Foreign Application Priority Data
Feb. 5, 2018   (KR) .................. 10-2018-0013842

(51) Int. Cl.
*A61B 5/024*   (2006.01)
*A61B 5/00*   (2006.01)
(Continued)

(52) U.S. Cl.
CPC ...... *A61B 5/02416* (2013.01); *A61B 5/02427* (2013.01); *A61B 5/0255* (2013.01);
(Continued)

(58) Field of Classification Search
CPC ............................. A61B 5/02416; A61B 5/00
See application file for complete search history.

(56) References Cited

U.S. PATENT DOCUMENTS 8,920,332 B2   12/2014   Hong et al.
8,956,303 B2   2/2015   Hong et al.
(Continued)

FOREIGN PATENT DOCUMENTS

JP   2005270661   10/2005
JP   2006061173   3/2006
(Continued)

OTHER PUBLICATIONS

PCT/ISA/210 Search Report issued on PCT/KR2019/000345, dated Apr. 23, 2019, pp. 5.
(Continued)

*Primary Examiner* — Angela M Hoffa
*Assistant Examiner* — Younhee Choi
(74) *Attorney, Agent, or Firm* — The Farrell Law Firm, P.C.

(57) ABSTRACT

An electronic device may include a PPG sensor including a light emitter that applies a current in a specified range and emits a light signal corresponding to the current and a light detector that amplifies a received light signal by applying one of a plurality of gain values, a memory that stores a plurality of sets of PPG models corresponding to the plu-
(Continued)

rality of gain values and including a current value and PPG level data corresponding to the current value, and at least one processor electrically connected to the PPG sensor and the memory.

12 Claims, 11 Drawing Sheets

(51) Int. Cl.
*A61B 5/0255* (2006.01)
*A61B 5/021* (2006.01)
(52) U.S. Cl.
CPC .......... *A61B 5/721* (2013.01); *A61B 5/02108* (2013.01); *A61B 5/02433* (2013.01); *A61B 2562/0219* (2013.01); *A61B 2562/0238* (2013.01)

(56) References Cited

U.S. PATENT DOCUMENTS

| | | | |
|---|---|---|---|
| 8,948,432 B2 | 3/2015 | Tanaka et al. | |
| 9,113,794 B2 | 8/2015 | Hong et al. | |
| 9,113,795 B2 | 8/2015 | Hong et al. | |
| 9,237,855 B2 | 1/2016 | Hong et al. | |
| 9,307,917 B2 | 4/2016 | Hong et al. | |
| 9,649,038 B2 | 5/2017 | Lee et al. | |
| 2014/0081153 A1 | 3/2014 | Kuno | |
| 2014/0275852 A1 | 9/2014 | Hong et al. | |
| 2015/0238095 A1 | 8/2015 | Lading et al. | |
| 2016/0360974 A1 | 12/2016 | Lange | |
| 2017/0105638 A1* | 4/2017 | Kulach | A61B 5/1118 |
| 2017/0143277 A1* | 5/2017 | Lisogurski | A61B 5/14551 |
| 2018/0317854 A1* | 11/2018 | Chao | A61B 5/02416 |

FOREIGN PATENT DOCUMENTS

| | | |
|---|---|---|
| JP | 2014057717 | 4/2014 |
| JP | 2014076273 | 5/2014 |
| KR | 1020160123321 | 10/2016 |

OTHER PUBLICATIONS

PCT/ISA/237 Written Opinion issued on PCT/KR2019/000345, dated Apr. 23, 2019, pp. 7.
European Search Report dated Jan. 21, 2021 issued in counterpart application No. 19747836.5-1115, 7 pages.

* cited by examiner

GRAPH 501: $y1 = m1(x) + n1$
GRAPH 503: $y2 = m2(x) + n2$

550
$y = 1/100(x) + 0.2$

600

ELECTRONIC DEVICE FOR ACQUIRING BIOMETRICS USING PPG SENSOR, AND METHOD THEREFOR

PRIORITY

This application is a national phase entry of PCT International Application No. PCT/KR2019/000315 which was filed on Jan. 9, 2019, and claims priority to Korean Patent Application No. 10-2018-0013842, which was filed on Feb. 5, 2018, the content of each of which is incorporated herein by reference.

BACKGROUND

1. Field

Embodiments disclosed herein relate to a technique for acquiring bio information based on a PPG signal.

2. Description of the Related Art

An electronic device capable of monitoring a user's bio information in real time has been provided as one form of health care. The user may measure bio information of the user by using a portable device such as a smart phone or a wearable device worn the user's body.

For example, a photoplethysmography (hereinafter referred to as PPG) sensor may measure a PPG signal from a user. An electronic device including a PPG sensor may acquire bio information including at least one of the heart rate, oxygen saturation ($SPO_2$), stress, arrhythmia, or blood pressure of the user by analyzing the PPG signal.

The PPG sensor may include a light emitter (e.g., LED) that emits light and a light detector (e.g., photo diode). The light emitter may emit light to tissues or blood vessels in the user's skin, and the light detector may collect the reflected light. The light collected by the light detector may be transformed into an electrical signal. The electrical signal may be referred to as a PPG signal. The electronic device may acquire bio information such as a heart rate and a blood pressure by analyzing the waveform of the PPG signal.

To obtain bio information from the PPG signal, the PPG signal needs to have an appropriate level. For example, when the PPG signal is saturated or a signal to noise ratio (SNR) is low, it may be difficult to extract bio information from the PPG signal.

The level of the PPG signal may be proportional to the intensity of light emitted by the light emitter and the intensity of light collected by the light detector. The intensity of light emitted by the light emitter may be proportional to the intensity of a current applied to the light emitter. The light detector may amplify the collected light according to a predetermined gain value.

The level of the acquired PPG signal may vary depending on the user even through a PPG sensor in which the current of the same intensity is applied and the same gain value is set. For example, even when the same amount of light is emitted from the light emitter, the darker the color of the skin, the smaller the intensity of reflected light may be. When the intensity of reflected light decreases, the level of the acquired PPG signal may decrease. Therefore, a current intensity and a gain value for acquiring bio information from the PPG signal may vary for different users. Therefore, the current intensity and the gain value may be determined differently to reach the same level of the PPG signal for different users, The electronic device may control a current value and a gain value to acquire an appropriate level of PPG signal for each user. The electronic device may perform multiple PPG measurements based on different current values and gain values to acquire an appropriate level of PPG signal. The electronic device may experimentally determine a current value and a gain value based on a plurality of pieces of PPG data acquired (automatic gain control (AGC)). However, when the AGC is repeatedly performed, a PPG signal delay or a PPG discontinuity occurs, and the PPG signal may be distorted. An error may occur in the bio information analyzed from the distorted PPG signal.

Embodiments disclosed herein provides an electronic device capable of controlling a current value and a gain value of a PPG sensor with a minimum number of times of performance to receive a PPG signal with an appropriate level according to a user.

SUMMARY

According to an embodiment disclosed herein, an electronic device may include a PPG sensor including a light emitter that applies a current in a specified range and emits a light signal corresponding to the current and a light detector that amplifies a received light signal by applying one of a plurality of gain values, a memory that stores a plurality of sets of PPG models corresponding to the plurality of gain values and including a current value and PPG level data corresponding to the current value, and at least one processor electrically connected to the PPG sensor and the memory, wherein the at least one processor may obtain a first PPG signal from the PPG sensor set with a first current value satisfying the specified range and a first gain value of the plurality of gain values when a user's contact is detected by the PPG sensor, generate a first PPG model corresponding to the user based on a first PPG model set corresponding to the first gain value among the plurality of sets of PPG models, the first current value and the first PPG signal, determine a second gain value and a second current value for obtaining a PPG signal with a specified PPG level, based at least on the first PPG model set, and obtain a second PPG signal with the specified PPG level using the PPG sensor set with the second gain value and the second current value.

Further, according to an embodiment disclosed herein, a method performed by an electronic device may include obtaining a first PPG signal from a PPG sensor using a first current value less than or equal to a maximum current value applicable to the PPG sensor and a first gain value of a plurality of gain values set in the PPG sensor when a user's contact is detected by the PPG sensor included in the electronic device, generating a first PPG model corresponding to the user based on a first PPG model set corresponding to the first gain value, the first current value, and the first PPG signal and obtaining a second PPG signal having a specified PPG level from the PPG sensor using a second gain value and a second current value determined based on a relationship between a current value corresponding to the specified PPG level specified in the first PPG level and a maximum current value.

Further, according to an embodiment disclosed herein, a computer recording medium storing computer readable instructions when is executed by at least one processor included in an electronic device, wherein the instructions cause the processor to obtain a first PPG signal from a PPG sensor using a first current value less than or equal to a maximum current value applicable to the PPG sensor, a first gain value of a plurality of gain values set in the PPG sensor, and a PPG DC offset value when a contact of a user is detected by the PPG sensor included in the electronic device, generate a first PPG model corresponding to the user based on a first PPG model set corresponding to the first gain value, the first current value, the first PPG signal, and the PPG DC offset value and obtain a second PPG signal having a specified PPG level from the PPG sensor using a second gain value and a second current value determined based on a relationship between a current value corresponding to the specified PPG level specified in the first PPG level and a maximum current value.

According to the embodiments disclosed herein, the electronic device may control the PPG sensor differently for different users, and acquire bio information through one time of measurement of the PPG signal.

In addition, various effects may be provided that are directly or indirectly understood through the disclosure.

BRIEF DESCRIPTION OF THE DRAWINGS

The above and other aspects, features, and advantages of the present disclosure will be more apparent from the following detailed description taken in conjunction with the accompanying drawings, in which.

DETAILED DESCRIPTION

Figure 1:
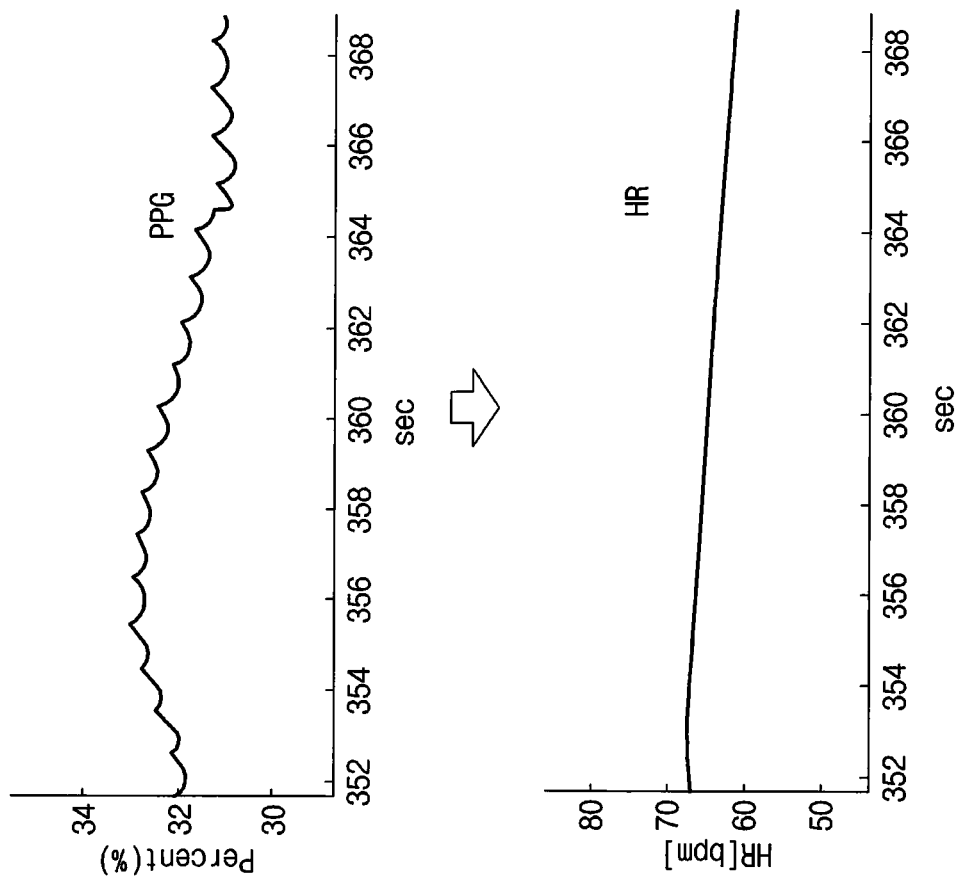
FIG. 1 illustrates an operating environment of an electronic device according to an embodiment.
Figure 1:
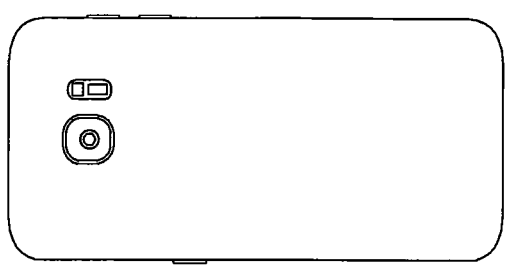
Figure 1:
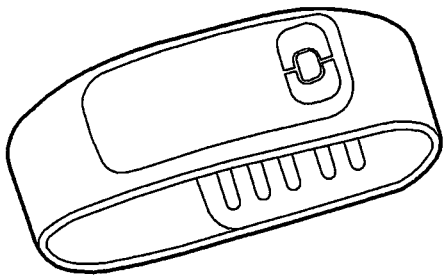

Hereinafter, various embodiments of the disclosure may be described with reference to accompanying drawings. Accordingly, those of ordinary skill in the art will recognize that modification, equivalent, and/or alternative on the various embodiments described herein can be variously made without departing from the scope and spirit of the disclosure. With regard to description of drawings, similar components may be marked by similar reference numerals.

In the disclosure, the expressions "have", "may have", "include" and "comprise", or "may include" and "may comprise" used herein indicate existence of corresponding features (e.g., components such as numeric values, functions, operations, or parts) but do not exclude presence of additional features.

In the disclosure, the expressions "A or B", "at least one of A or/and B", or "one or more of A or/and B", and the like may include any and all combinations of one or more of the associated listed items. For example, the term "A or B", "at least one of A and B", or "at least one of A or B" may refer to all of the case (1) where at least one A is included, the case (2) where at least one B is included, or the case (3) where both of at least one A and at least one B are included.

The terms, such as "first", "second", and the like used in the disclosure may be used to refer to various components regardless of the order and/or the priority and to distinguish the relevant components from other components, but do not limit the components. For example, "a first user device" and "a second user device" indicate different user devices regardless of the order or priority. For example, without departing the scope of the disclosure, a first component may be referred to as a second component, and similarly, a second component may be referred to as a first component.

It will be understood that when an component (e.g., a first component) is referred to as being "(operatively or communicatively) coupled with/to" or "connected to" another component (e.g., a second component), it may be directly coupled with/to or connected to the other component or an intervening component (e.g., a third component) may be present. In contrast, when an component (e.g., a first component) referred to as being "directly coupled with/to" or "directly connected to" another component (e.g., a second component), it should be understood that there are no intervening component (e.g., a third component).

According to the situation, the expression "configured to" used in the disclosure may be used as, for example, the expression "suitable for", "having the capacity to", "designed to", "adapted to", "made to", or "capable of". The term "configured to" must not mean only "specifically designed to" in hardware. Instead, the expression "a device configured to" may mean that the device is "capable of" operating together with another device or other parts. For example, a "processor configured to (or set to) perform A, B, and C" may mean a dedicated processor (e.g., an embedded processor) for performing a corresponding operation or a generic-purpose processor (e.g., a central processing unit (CPU) or an application processor) which performs corresponding operations by executing one or more software programs which are stored in a memory device.

Terms used in the disclosure are used to describe specified embodiments and are not intended to limit the scope of the disclosure. The terms of a singular form may include plural forms unless otherwise specified. All the terms used herein, which include technical or scientific terms, may have the same meaning that is generally understood by a person skilled in the art. It will be further understood that terms, which are defined in a dictionary and commonly used, should also be interpreted as is customary in the relevant related art and not in an idealized or overly formal unless expressly so defined in various embodiments of the disclosure. In some cases, even if terms are terms which are defined in the disclosure, they may not be interpreted to exclude embodiments of the disclosure.

An electronic device according to various embodiments of the disclosure may include at least one of, for example, smartphones, tablet personal computers (PCs), mobile phones, video telephones, electronic book readers, desktop PCs, laptop PCs, netbook computers, workstations, servers, personal digital assistants (PDAs), portable multimedia players (PMPs), Motion Picture Experts Group (MPEG-1 or MPEG-2) Audio Layer 3 (MP3) players, mobile medical devices, cameras, or wearable devices. According to various embodiments, the wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit).

According to various embodiments, the electronic device may be a home appliance. The home appliances may include at least one of, for example, televisions (TVs), digital versatile disc (DVD) players, audios, refrigerators, air conditioners, cleaners, ovens, microwave ovens, washing machines, air cleaners, set-top boxes, home automation control panels, security control panels, TV boxes (e.g., Samsung HomeSync™, Apple TV™, or Google TV™), game consoles (e.g., Xbox™ or PlayStation™), electronic dictionaries, electronic keys, camcorders, electronic picture frames, and the like.

According to another embodiment, an electronic device may include at least one of various medical devices (e.g., various portable medical measurement devices (e.g., a blood glucose monitoring device, a heartbeat measuring device, a blood pressure measuring device, a body temperature measuring device, and the like), a magnetic resonance angiography (MRA), a magnetic resonance imaging (MRI), a computed tomography (CT), scanners, and ultrasonic devices), navigation devices, Global Navigation Satellite System (GLASS), event data recorders (EDRs), flight data recorders (FDRs), vehicle infotainment devices, electronic equipment for vessels (e.g., navigation systems and gyrocompasses), avionics, security devices, head units for vehicles, industrial or home robots, automated teller machines (ATMs), points of sales (POSs) of stores, or internet of things (e.g., light bulbs, various sensors, electric or gas meters, sprinkler devices, fire alarms, thermostats, street lamps, toasters, exercise equipment, hot water tanks, heaters, boilers, and the like).

According to an embodiment, the electronic device may include at least one of parts of furniture or buildings/structures, electronic boards, electronic signature receiving devices, projectors, or various measuring instruments (e.g., water meters, electricity meters, gas meters, or wave meters, and the like). According to various embodiments, the electronic device may be one of the above-described devices or a combination thereof. An electronic device according to an embodiment may be a flexible electronic device. Furthermore, an electronic device according to an embodiment of the disclosure may not be limited to the above-described electronic devices and may include other electronic devices and new electronic devices according to the development of technologies.

Hereinafter, electronic devices according to various embodiments will be described with reference to the accompanying drawings. In the disclosure, the term "user" may refer to a person who uses an electronic device or may refer to a device (e.g., an artificial intelligence electronic device) that uses the electronic device.

FIG. 1 illustrates an operating environment of an electronic device according to an embodiment.

Referring to FIG. 1, an electronic device 100 and a PPG sensor included in the electronic device 100 (e.g., a PPG sensor 200 of FIG. 2) may be included.

In one embodiment, the electronic device 100 may be referred to as a portable device such as a smart phone or a wearable device such as a smart watch or smart band. A user may estimate bio information such as heart rate, oxygen saturation ($SPO_2$), stress, and blood pressure using the PPG sensor included in the electronic device 100. The electronic device 100 may be referred to as a user terminal.

The electronic device 100 may analyze a PPG signal acquired and acquire bio information. Therefore, the PPG signal may need to have an appropriate level to extract bio information. For example, the higher the level of the PPG signal, the greater the signal to noise ratio (SNR) of the PPG signal. However, when power consumed by the PPG sensor increases and the PPG signal is out of a reception range of a photo detector, the PPG signal may be saturated. When the PPG signal is saturated, it may be difficult to determine information related to bio information in a waveform of the PPG signal. On the other hand, as the level of the PPG signal decreases, the information related to the bio information may fall below a noise level of the sensor, and the SNR may decrease. The appropriate level of the PPG signal, which is able to include bio information, may vary for different users. For example, the appropriate level may be specified for each user in advance.

In various embodiments, an appropriate PPG level for each user (target PPG level) may be specified in advance in consideration of the SNR of the PPG signal or the power consumption of the PPG sensor. The target PPG level may be specified for each user according to statistical data. For example, the target PPG level may be specified to be a value in a range between a low limit threshold and a high limit threshold. For example, when it is determined that the user's movement is not large (e.g., sleep), the electronic device 100 may specify the low limit threshold, at which an SNR is guaranteed, as a target level to lower power consumption. For example, when it is determined that the user's movement is large (e.g., exercise), the electronic device 100 may specify the high limit threshold as a target level to increase the SNR. Hereinafter, it is assumed that appropriate PPG levels are specified in advance for different users.

Hereinafter, the bio information will be described by taking a heart rate as an example. However, the disclosure is not limited thereto, and may include all types of bio information that may be extracted from the PPG signal.

Figure 2:
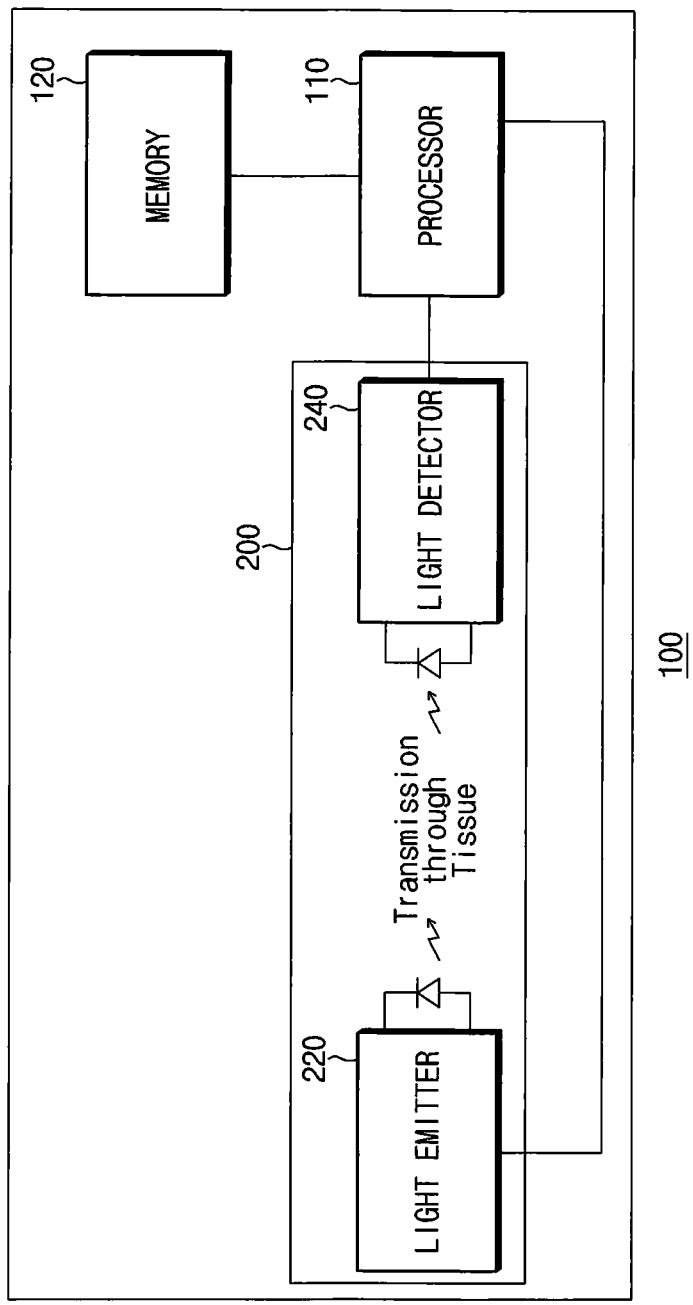
FIG. 2 is a block diagram of an electronic device according to an embodiment.

FIG. 2 is a block diagram of an electronic device according to an embodiment.

Referring to FIG. 2, the electronic device 100 according to an embodiment may include a processor 110, a memory 120, and the PPG sensor 200. The processor 110 may be electrically connected to the memory 120 and the PPG sensor 200. The processor 110 may directly or indirectly control the memory 120 and the PPG sensor 200. For example, the processor 110 may be referred to as an application processor.

In one embodiment, the PPG sensor 200 may include a light emitter 220 and a light detector 240. When a current is applied, the light emitter 220 may emit a light signal having an intensity corresponding to the intensity of the applied current. For example, the light emitter 220 may include a light emitting diode (LED). The maximum current of capable of being applied to the light emitter 220 may be determined according to hardware specifications of the light emitter 220. The light detector 240 may receive a light signal reflected in such a manner that the light signal emitted from the light emitter 220 is reflected on an external object. The light detector 240 may amplify the received light signal according to a set gain value. For example, a plurality of gain values that may be set in the light detector 240 may be predetermined in advance. The light detector 240 may be set to amplify the received light signal according to one of the plurality of predetermined gain values.

For example, the processor 110 may apply a current smaller than the maximum current to the light emitter 220 and allow the light emitter to emit a light signal according to the applied current. For example, the magnitude of a current that may be applied to the light emitter 220 may be specified in a predetermined range in advance. The processor 110 may perform control to amplify the light signal received through the light detector 240 using one of the plurality of preset gain values.

In one embodiment, the memory 120 may include a plurality of sets of PPG models. The plurality of sets of PPG models may include a plurality of PPG models corresponding to a plurality of users. Depending on users, the level of the PPG signal acquired may vary according to a current value applied to the PPG sensor 200 and a gain value. Each PPG model may include PPG data corresponding to any one user. The PPG data may be referred to as the level of the PPG signal according to the current value and the gain value.

For example, the plurality of sets of PPG models may include a set of PPG models corresponding to each of a plurality of gain values determined in advance for the light detector 240 of the PPG sensor 200. The plurality of sets of PPG models may include a level value of a PPG signal corresponding to a current value for one gain value.

In one embodiment, when it is detected that an arbitrary user wears the electronic device 100, the electronic device 100 may acquire a first PPG signal from the PPG sensor 200 set with a first current value and a first gain value. For example, the first current value may be specified to be a value less than the maximum current that may be applied to the light emitter 220. The first gain value may be set to one of a plurality of gain values.

In one embodiment, the electronic device 100 may generate a first PPG model corresponding to the arbitrary user based on a first PPG model set corresponding to the first gain value, the first current value, and the first PPG signal. For example, the first PPG model may include a PPG level value according to a gain value and a current value for the arbitrary user.

In one embodiment, the electronic device 100 may determine a second current value and a second gain value for acquiring a PPG signal with a specified PPG level, based at least on the first PPG model set. For example, the electronic device 100 may determine a second gain value based on a relationship between a current value corresponding to the PPG level specified in the generated first PPG model set and the maximum current value that may be applied to the light emitter 220. The electronic device 100 may acquire a first PPG signal (e.g., a final PPG signal) having a specified PPG level from the PPG sensor 200 using the second gain value and a current value corresponding to the specified PPG level.

In various embodiments, the electronic device 100 may extract bio information from the first PPG signal.

Figure 3:
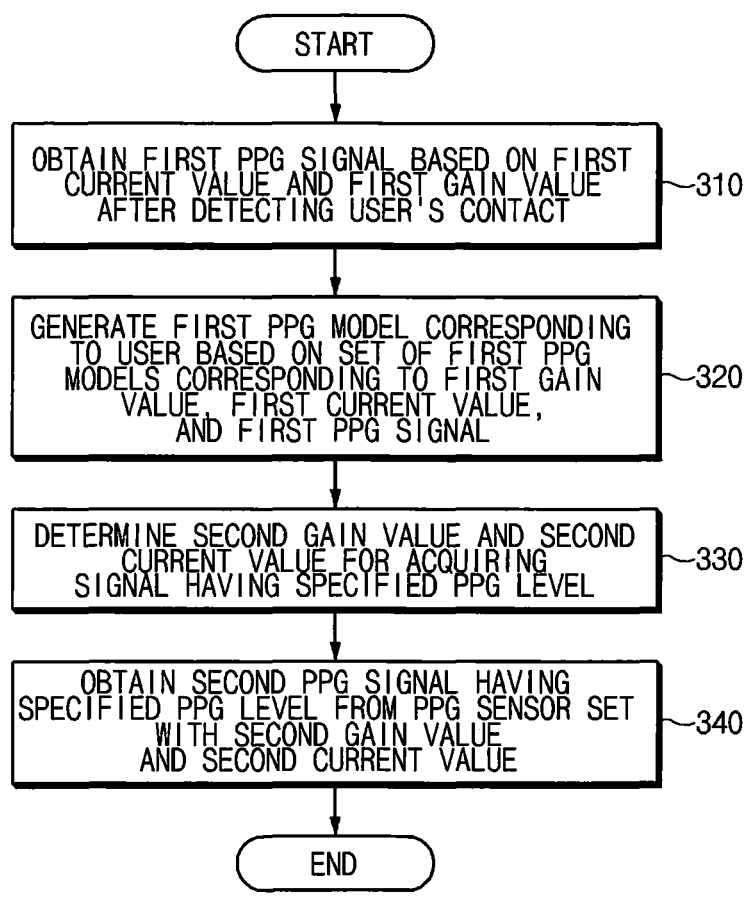
FIG. 3 is a flowchart of a method of acquiring a PPG signal having a specified PPG level according to an embodiment.
Figure 4:
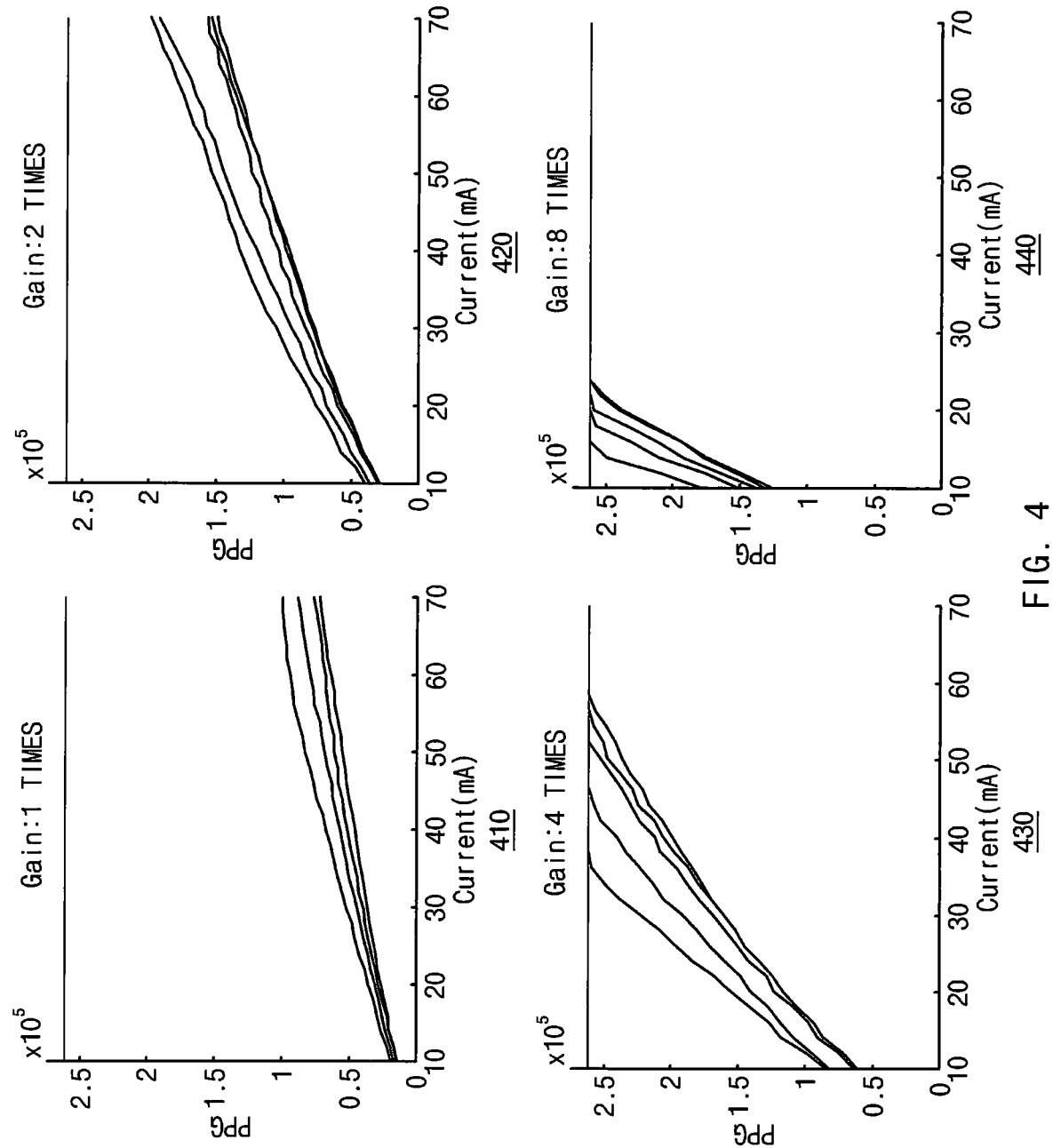
FIG. 4 is a diagram illustrating an example of a plurality of sets of PPG models for a plurality of users according to various embodiments.
Figure 5:
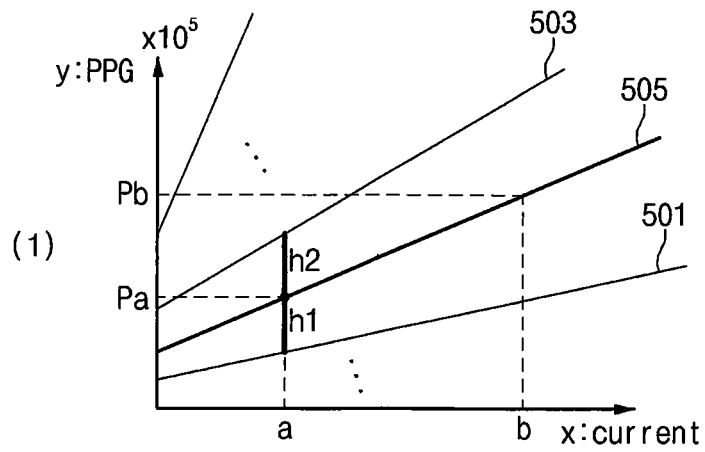
FIG. 5 is a diagram for describing a method for generating a PPG model corresponding to an arbitrary user according to an embodiment.
Figure 5:
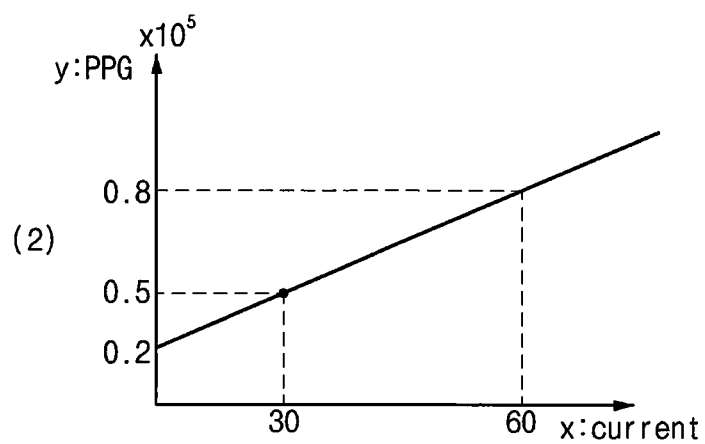
Figure 5:
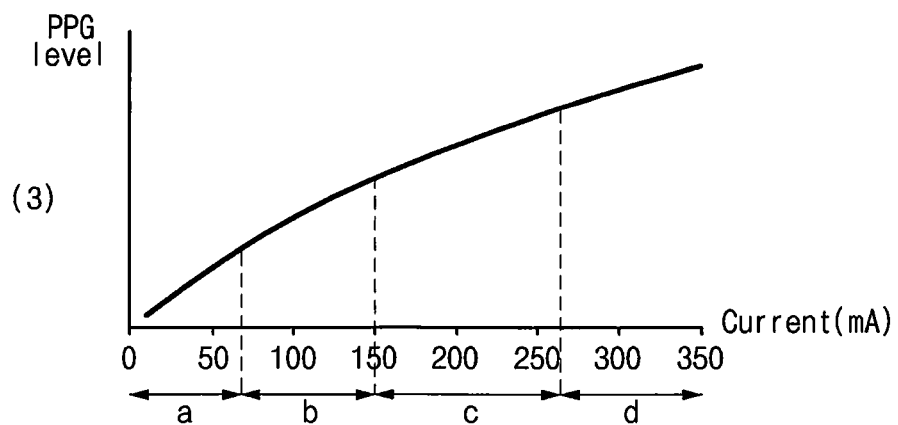

FIG. 3 is a flowchart of a method of acquiring a PPG signal having a specified PPG level according to an embodiment. FIG. 4 is a diagram illustrating an example of a plurality of sets of PPG models according to various embodiments. FIG. 5 is a diagram for describing a method for generating a PPG model corresponding to an arbitrary user according to an embodiment. Hereinafter, a method of acquiring a PPG signal having a specified PPG level will be described with reference to FIGS. 3 to 5.

Referring to FIG. 3, a method of acquiring a PPG signal having a specified PPG level according to an embodiment may include operations 310 to 340. The operations 310 to 340 may be performed, for example, by the electronic device 100 illustrated in FIG. 2. Each of the operations 310 to 340 may be implemented as instructions (commands) that may be performed (or executed) by the processor 110 of the electronic device 100, for example. The instructions may be stored in, for example, a computer recording medium or the memory 120 of the electronic device 100 shown in FIG. 2. Hereinafter, a description overlapping with the description with reference to FIG. 2 may be omitted.

The electronic device 100 according to an example cited in the description with reference to FIG. 3 may be assumed to have the following setting values. For example, the light emitter 220 of the PPG sensor 200 may receive a current of about 20 mA to about 70 mA, and the maximum current value may be set to about 70 mA. For example, the gain value of the light detector 240 may be set in four phases (e.g., '11', '10', '01', and '00'). For example, the light detector 240 may amplify the received light signal by 1 time, 2 times, 4 times, and 8 times respectively when the gain value is '00', '01', '10', and '11'.

In one embodiment, the plurality of sets of PPG models may include a set of PPG models corresponding to each of a plurality of gain values predetermined for the light detector 240. For example, each PPG model may be stored in the memory 120 as data including a gain value and a current value, and a PPG level value. According to an embodiment, at least a part of the sets of PPG models may be received or updated from an external electronic device (e.g., a server 1008 of FIG. 10) using a communication module (e.g., a communication module 1090 of FIG. 10).

Referring to FIG. 4, each PPG model may be expressed by a graph. For example, each of the PPG models may be referred to as a first-order function having a current value on an x-axis and a level value of the acquired PPG signal on a y-axis. The PPG model may be expressed by a straight line graph. For example, each PPG model may be stored in the memory 120 of the electronic device 100 as a y-intercept value and a slope value corresponding to the PPG model.

For example, a first graph 410 may represent a plurality of PPG models including PPG data measured according to the current value when the gain value is '00' (e.g., phase 1). A plurality of PPG models corresponding to one gain value may be referred to as one set of PPG models. The first graph 410 may represent a set of PPG models corresponding to the gain value '00'. A second graph 420 may represent a plurality of PPG models including PPG data measured according to the current value when the gain value is '01' (e.g., phase 2). A third graph 430 may represent a plurality of PPG models including PPG data measured according to the current value when the gain value is '10' (e.g., phase 3). A fourth graph 440 may represent a plurality of PPG models including PPG data measured according to the current value when the gain value is '11' (e.g., phase 4).

In operation 310, when the electronic device 100 detects a user's contact, the electronic device 100 may acquire a first PPG signal from the PPG sensor 200 set with the first current value and the first gain value.

In various embodiments, the electronic device 100 may perform PPG measurement when detecting the user's contact. For example, when the electronic device 100 is a smart phone, PPG measurement may be performed when an approach of a part of the user's body, such as a finger, to the PPG sensor 200 of the smart phone is detected. For example, when the electronic device 100 is a wearable device, PPG measurement may be performed when it is detected that the wearable device is worn on the user's body. The PPG sensor 200 included in the wearable device may be configured to contact the user's body when the wearable device is worn on the user's body.

In various embodiments, the wearable device may not perform PPG measurement according to the wearing posture even when wearing is detected. Related embodiments will be described later with reference to FIG. 10.

For example, when the first current value is about 30 mA and the first gain value is '00' (e.g., phase 1), the level of the first PPG signal acquired may be 0.5.

In operation 320, the electronic device 100 may generate a first PPG model corresponding to the user based on the first PPG model set corresponding to the first gain value, the first current value, and the first PPG signal.

For example, when the first current value is about 30 mA and the first gain value is '00' (e.g., phase 1), the electronic device 100 may refer to a first graph 410 corresponding to the first gain value '00'. The electronic device 100 may select two closest models from among a plurality of models included in the first graph 410 based on the first current value and the first PPG signal.

For example, referring to FIG. 5, the level Pa of the first PPG signal measured with respect to the first current value (a) is illustrated. Among the plurality of models included in a graph 500, two models closest to point (a, Pa) may be selected. For example, a second PPG model 501 and a third PPG model 503 having the closest vertical distances h1 and h2 from point (a, Pa) may be selected.

In one embodiment, the electronic device 100 may generate a first PPG model corresponding to the user with reference to the second PPG model 501 and the third PPG model 503. For example, a slope (m) of the first PPG model 505 may be calculated by substituting the slope (m1) of the second PPG model 501, the slope (m2) of the third PPG model 503, the vertical distance (h1) from point (a, Pa) to the second PPG model 501 and the vertical distance (h2) from point (a, Pa) to the third PPG model 503 to the internally dividing point. That is, the slope (m) may be determined to be a result value of (h1*m2+h2*m1)/(h1+h2) that divides the slope (m1) of the second PPG model 501 and the slope (m2) of the third PPG model 503 into h1 and h2. The first PPG model 505 may be referred to as a straight line function passing through point (a, Pa) with the slope (m). The first PPG model 505 may be expressed as a first-order function y=m (x−a)+Pa. This model interpolation may be very useful to express a relationship between a current and a. PPG for each gain value. When the relationship between the current and the PPG is expressed as a table for a specific gain value, it is inefficient in terms of computational amount because it requires not only a lot of memory when implementing it with real codes, but also a separate search algorithm to find out solutions. The proposed model interpolation ensures the uniqueness of the solution from the experimental conclusion that the PPG value according to the current is approximated to the first-order equation within the specified current section and the two different first-order equations do not intersect each other. That is, the current value corresponding to the specified PPG level may always be mathematically calculated using the inverse function of the first-order function without a separate search algorithm.

In operation 330, the electronic device 100 may determine a second gain value and a second current value based on a relationship between a current value corresponding to the PPG level specified according to the generated first PPG model and the maximum current value that may be applied to the light emitter 220.

In one embodiment, the electronic device 100 may determine a current value corresponding to a PPG level specified from the first PPG model 505. For example, referring to FIG. 5, the electronic device 100 may determine the current value corresponding to the specified PPG level Pb as "b" using the first PPG model 505.

In operation 330, for example, the electronic device 100 may compare a current value corresponding to the specified PPG level with the maximum current value that may be applied to the light emitter 220.

In one embodiment, when the current value corresponding to the specified PPG level is determined to be a value less than or equal to the maximum current value, the electronic device 100 may maintain the first gain value. In this case, the first gain value may be determined to be the second gain value, and the current value corresponding to the specified PPG level may be determined to be the second current value. The electronic device 100 may set the second gain value to the first gain value, and may set the second current value to the first current value.

In one embodiment, when the current value corresponding to the specified PPG level is determined to be a value exceeding the maximum current value, the electronic device 100 may increase the gain value of the light detector 240. The electronic device 100 cannot apply a current exceeding the maximum current value to the light emitter 220. The reason for this is that the light emitter 220 has the maximum current value capable of being applied due to the characteristics of hardware. Since the current value, the gain value and the PPG level are proportional to one another, the electronic device 100 may lower the current value by increasing the gain value. The electronic device 100 may set the second gain value to a value greater than the first gain value, and may set the second current value to a value less than the maximum current value and corresponding to the second gain value. For example, when the gain value is set from 1 times to 2 times, 4 times, or 8 times, current values corresponding to ½ times, ¼ times, and ⅛ times the specified PPG level may need to be set. The relationship between the current and the PPG may be approximated to a linear equation within a specific current section through statistical analysis of experimental data. The value corresponding to the second gain value may be referred to as a current value capable of acquiring a PPG signal correspond to a changed second gain value and having a specified PPG level. The current value may be experimentally determined by referring to statistical data on a change in the level of the PPG signal according to a change in the gain value and the current value. The electronic device 100 may refer to, for example, a data set including a level value of a PPG signal acquired corresponding to a specific gain value predetermined for each type of the PPG sensor 200 and a specific current value. The data set may be stored in the electronic device 100 in advance or may be acquired from or updated by an external device (e.g., server). The electronic device 100 may determine a current value to be set corresponding to the gain value changed by referring to the data set.

In one embodiment, when the current value corresponding to the specified PPG level is less than a pre-specified value associated with the maximum current value, the electronic device 100 may set the second gain value to a value less than the first gain value, and the second current value to a value greater than a current value corresponding to the specified PPG level and corresponding to the second gain value. For example, the electronic device 100 may be configured to lower the second gain value when the current value corresponding to the specified PPG level is less than ½ of the maximum current value. The electronic device 100 may set the second current value to a current value corresponding to the lowered second gain value. For example, when the gain value is set from 8 times to 4 times, 2 times, or 1 times, the current values corresponding to 2 times, 4 times, and 8 times of the specified PPG level may need to be set and may need not to exceed the maximum current supported by the electronic device 100. The relationship between the current and the PPG may be approximated to a linear equation within a specific current section through statistical analysis of experimental data.

Referring to graph (2) of FIG. 5, the generated first PPG model 550 is illustrated. The generated first PPG model 550 was illustrated as a first-order function with a slope of $\frac{1}{100}$ and a y-intercept of 0.2. When the first current value is 30 mA and the first gain value is 00, that is, 1 times, it may be assumed that the level of the acquired PPG signal is 0.5 and the specified PPG level is 1.2.

For example, the electronic device 100 may determine a current value corresponding to 1.2, which is the PPG level specified according to the first PPG model 550, as 100 mA. However, when the maximum current value is assumed to be 70 mA, the second current value may need to be set to be less than 100 mA. For example, the electronic device 100 may change the gain value of the light detector 240 to '01', that is, 2 times. The electronic device 100 may set a value corresponding to the changed gain value and less than the maximum current value of 70 mA as the second current value.

In one embodiment, when the current value corresponding to the PPG level 1.2 specified in the first PPG model 550 is specified to be 100 mA and the value is out of the maximum current value, the gain value may be specified to be 2 times the gain value and a current value 40 mA corresponding to 0.6 that is ½ times the specified PPG level may be specified.

In one embodiment, when the current value corresponding to the PPG level 2.8 specified in the first PPG model 550 is specified to be 260 mA and the value is out of the maximum current value, the gain value may be specified to be 4 times the gain value and a current value 50 mA corresponding to 0.7 that is ¼ times the specified PPG level may be specified.

In operation 340, the electronic device 100 may acquire a second PPG signal having the specified PPG level from the PPG sensor 200 using the second gain value and the second current value which are determined. The electronic device 100 may determine a final gain value (e.g., the second gain value) and a final current value (e.g., the second current value) corresponding to a specific user by measuring the PPG signal once, and acquire a final PPG signal (e.g., the second PPG signal) including bio information. The electronic device 100 may extract heart rate information from the final PPG signal having the specified PPG level.

In various embodiments, there may occur a case in which two similar models cannot be selected from among a plurality of PPG models included in a set of PPG models corresponding to the first gain value, based on the first current value and the first PPG signal. For example, there may occur a case in which the level of the first PPG signal measured initially is not located between the plurality of models and has a higher level or a lower level than the plurality of models. In this case, the electronic device 100 may add the PPG data of a corresponding user to the set of PPG models as a new model.

For example, PPG measurement may be further performed on the user using the first gain value and another current value different from the first current value. The electronic device 100 may calculate a first-order function corresponding to the PPG model based on the data of the first current value and the first PPG signal, and the other current value and the PPG signal additionally acquired. The newly calculated first-order function may be added to the set of PPG models.

In various embodiments, to improve the accuracy of the heart rate estimated from the measured PPG, it is possible to increase a current and a gain within a range in which the PPG signal is not saturated. For example, in a situation in which a time for measuring the PPG signal is not long and power consumption is not required to be considered, raising the current rather than raising the gain may be advantageous in maximizing the SNR of a heart rate signal included in the PPG signal.

Referring to (3) of FIG. 5, a graph showing a change in the level value of the PPG signal when the current intensity increases is illustrated. As the magnitude of the current applied to the light emitter 220 increases, the increase width in the level of the PPG signal decreases and therefore, the graph of the level of the PPG signal with respect to the current may be drawn non-linearly. However, the entire current section may be represented by several linear sections. For example, the graph (3) may be divided into sections "a" to "d", and each section may be approximated to a linear graph.

For example, "a" section in which the current changes from about 10 mA to about 70 mA may be approximated to a linear graph because the rate of the amount of increase in the PPG level according to the amount of increase in the current is similar regardless of the current values. For the entire current section of graph (3), uniqueness for the value of the PPG level corresponding to a specific current value may be ensured. The curve graphs of sections "a" to "d" of graph (3) each may be approximated to a linear graph.

In various embodiments, each model included in the PPG model set may be referred to as one linear graph summing sections each approximated to the linear graph. For example, the linear graphs approximated in sections "a" to "d" of the graph (3) may be summed, and a linear graph of the entire current section from the section "a" to the section "d" may be derived.

Figure 6:
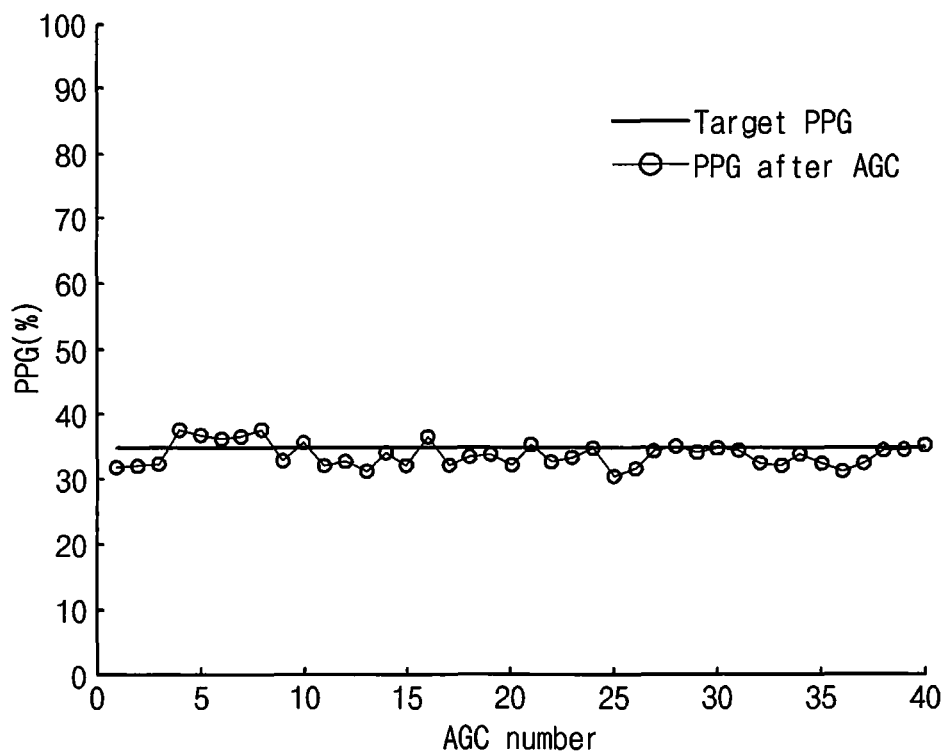
FIG. 6 shows experimental data of a PPG signal measured according to an embodiment.

FIG. 6 shows experimental data of a PPG signal measured according to an embodiment. Referring to FIG. 6, experimental data 600 acquired by collecting PPG signals according to a method of acquiring a PPG signal having a specified PPG level according to an embodiment of the disclosure is illustrated.

It is represented that the PPG signals acquired from the experimental data 600 mostly have levels adjacent to a specified PPG level. In a relevant experimental example, the error rate was measured to be about 1.848%, and the maximum error rate was measured to be about 0.4.414%.

Figure 7A:
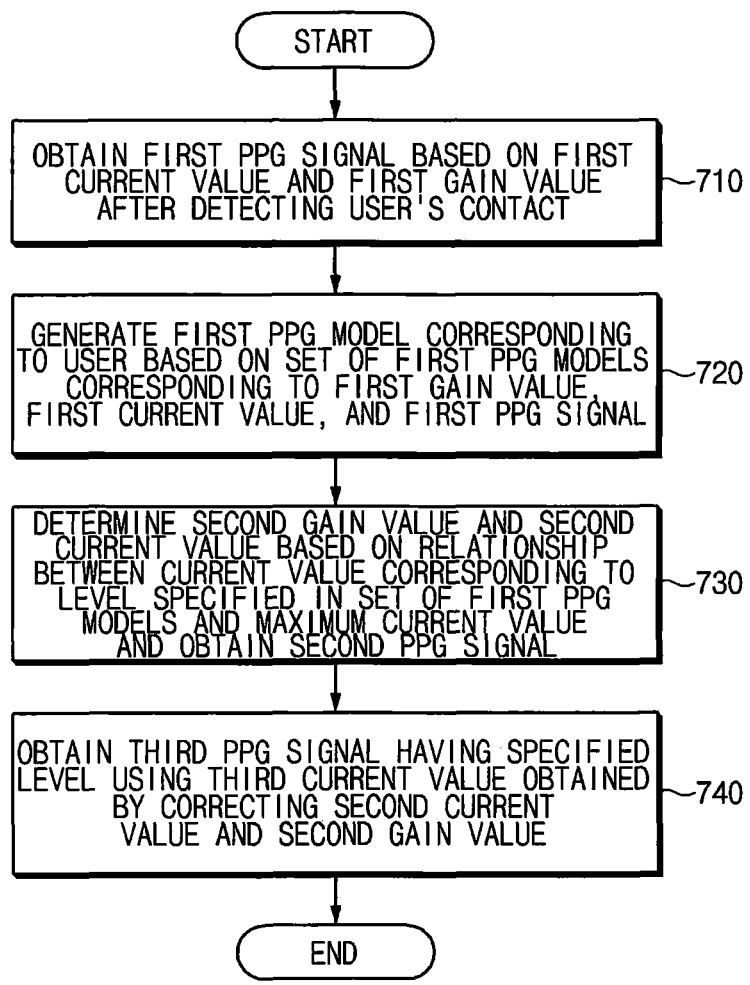
FIG. 7A is a flowchart of a method of correcting a PPG signal according to an embodiment.
Figure 7B:
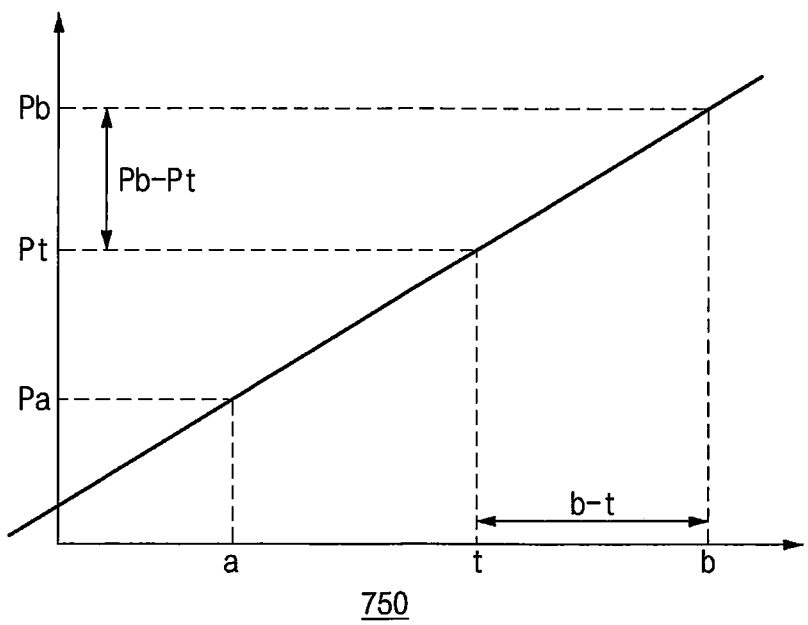
FIG. 7B is a diagram for describing a method of correcting a PPG signal according to an embodiment.

FIG. 7A is a flowchart of a method of correcting a PPG signal according to an embodiment. FIG. 7B is a diagram for describing a method of correcting a PPG signal according to an embodiment. Hereinafter, a method of correcting a PPG signal will be described with reference to FIGS. 7A and 7B.

Referring to FIG. 7A, a method of acquiring a PPG signal having a specified PPG level according to an embodiment may include operations 710 to 740. The operations 710 to 740 may be performed, for example, by the electronic device 100 illustrated in FIG. 2. Each of the operations 710 to 740 may be implemented as instructions (commands) that may be performed (or executed) by the processor 110 of the electronic device 100, for example. The instructions may be stored in, for example, a computer recording medium or the memory 120 of the electronic device 100 shown in FIG. 2. Operations 710 to 730 may correspond to operations 310 to 330 of FIG. 3. Hereinafter, reference numerals of FIG. 2 are used to describe operations 710 to 740, and descriptions overlapping with those with reference to FIG. 2 may be omitted.

In operation 710, when the electronic device 100 detects that a user wears the electronic device 100, the electronic device 100 may acquire a first PPG signal from the PPG sensor 200 set with the first current value and the first gain value.

In various embodiments, even when the PPG signal is acquired based on the same current value and gain value, the PPG level value of the PPG signal acquired may vary according to the user wearing state (e.g., the user's operating state, the user's posture) Therefore, the electronic device 100 may acquire a temporary PPG signal based on the first current value and the first gain value after it is detected that user wears the electronic device. The electronic device 100 may determine the acquired PPG signal as a first PPG signal within a stabilization section in which a change width of the acceleration of the electronic device 100 is less than or equal to a specific threshold value and a change width of the temporary PPG level is less than or equal to a specific threshold value. For example, the specific threshold value for the change width of the acceleration and the specific threshold value for the change width of the PPG level may be determined in advance by experiment. For example, the change in acceleration may be measured by an acceleration sensor included in the electronic device 100.

In operation 720, the electronic device 100 may generate a first PPG model corresponding to the user based on the first PPG model set corresponding to the first gain value, the first current value, and the first PPG signal.

In operation 730, the electronic device 100 may determine a second gain value and a second current value based on a relationship between a current value corresponding to the PPG level specified according to the generated first PPG model and the maximum current value that may be applied to the light emitter 220. The electronic device 100 may acquire the second PPG signal from the PPG sensor 200 using the second gain value and the second current value which are determined.

For example, the second gain value and the second current value may be referred to as the second gain value and the second current value in operation 330 of FIG. 3. The electronic device 100 may acquire the second PPG signal using the second gain value and the second current value determined in operation 730. In various embodiments, an error rate may be improved by correcting the acquired PPG signal.

In operation 740, the electronic device 100 may acquire a third PPG signal having a specified PPG level from the PPG sensor using a third current value obtained by correcting the second current value and the second gain value.

In one embodiment, the electronic device 100 may correct a current value using the first current value, the first PPG signal, the second current value, and the second PPG signal.

Referring to FIG. 7B, an example is illustrated in which a level of the first PPG signal corresponding to the first current value "a" is Pa and a level of the second PPG signal corresponding to the second current value "b" is Pb. It may be assumed that the specified PPG level is Pt, and a difference between Pb−Pt occurs as an error.

For example, the amount of increase in the level of the PPG signal corresponding to the increased current value may be different for different users. Through two points (a, Pa) and (b, Pb), the ratio of the amount of increase in the current to the amount of increase in the PPG level may be determined for a specific user. In graph 750 of FIG. 7B, it is illustrated that the amount of increase in the current is (b−a) and the amount of increase in the PPG level is (Pb−Pa). Therefore, the ratio may be referred to as (b−a)/(Pb−Pa).

For example, the electronic device 100 may determine a third current value for acquiring a signal with the specified PPG level using the ratio. Assuming that the ratio is unique for each user, a value "t" may be calculated using the formula (b−a)/(Pb−Pa)=(b−t)/(Pb−Pt).

For another example, the electronic device 100 may generate a corrected first PPG model corresponding to the user using two points (a, Pa), and (b, Pb). For example, a first-order function passing through the two points may be referred to as a corrected first PPG model. The electronic device 100 may determine a current value "t" for acquiring the third PPG signal having a level Pt, which is the specified PPG level, from the corrected first PPG model.

In various embodiments, when there are no a plurality of sets of PPG models (e.g., PPG models 501 and 503 of FIG. 5) by statistical analysis, a PPG model corresponding to a user may be generated with reference to FIG. 7B. For example, there may be a case where the first PPG model 505 cannot be generated because there are no a plurality of PPG models in FIG. 5.

In this case, the electronic device 100 may generate an approximate first-order function having a slope of Pa/a and passing through the origin as a PPG model corresponding to a specific user (e.g., the first PPG model 505 of FIG. 5). When the current "b" corresponding to the level Pt, which is the PPG level specified from the PPG model, is specified and the actually-measured level of the PPG signal is Pb, the electronic device 100 may generate a PPG model corresponding to the user using two points (a, Pa) and (b, Pb). It is possible to determine the current "t" corresponding to the level Pt, which is the PPG level specified from the generated PPG model. For comparison, according to the method using the model interpolation described above with reference to FIG. 5, it is possible to acquire a PPG signal having a specified PPG level even when the AGC is performed only once, and according to the method according to various embodiments, it is possible to acquire the PPG signal having the PPG level specified through two AGCs.

In one embodiment for FIG. 7B, the specified PPG level, Pt, may be specified to be various values, and it is possible to increase the specified PPG level to increase the SNR of the heart rate signal included in the PPG value, and decrease the specified PPG level to low power consumption when motion artifacts due to movement is small as in sleep situations. When the PPG value falls within a specific range around the specified PPG level after the initial AGC is performed, it is possible to widen the range to prevent the AGC from being frequently performed according to a change in the user's posture or the user's wearing state. For example, the PPG level specified in the initial AGC operation may be specified to be 70% of the maximum PPG level, and when the PPG value falls within the range of ∈8% around the specified PPG level immediately after the AGC is performed, the initial AGC is finished. Thereafter, when the PPG value is out of the range of ±28% around the specified PPG level according to a change in posture or the wearing state, AGC may be performed to acquire the specified PPG level by changing the current value or the gain value.

In various embodiments, when the corrected third current value is greater than the maximum current value, the electronic device 100 may determine a third gain value that is a value greater than the second gain value, and determine the third current value to be a fourth current value less than the maximum current value and corresponding to the third gain value. The electronic device 100 may acquire a third PPG signal having the specified PPG level from the PPG sensor using the third gain value and the fourth current value.

Figure 8:
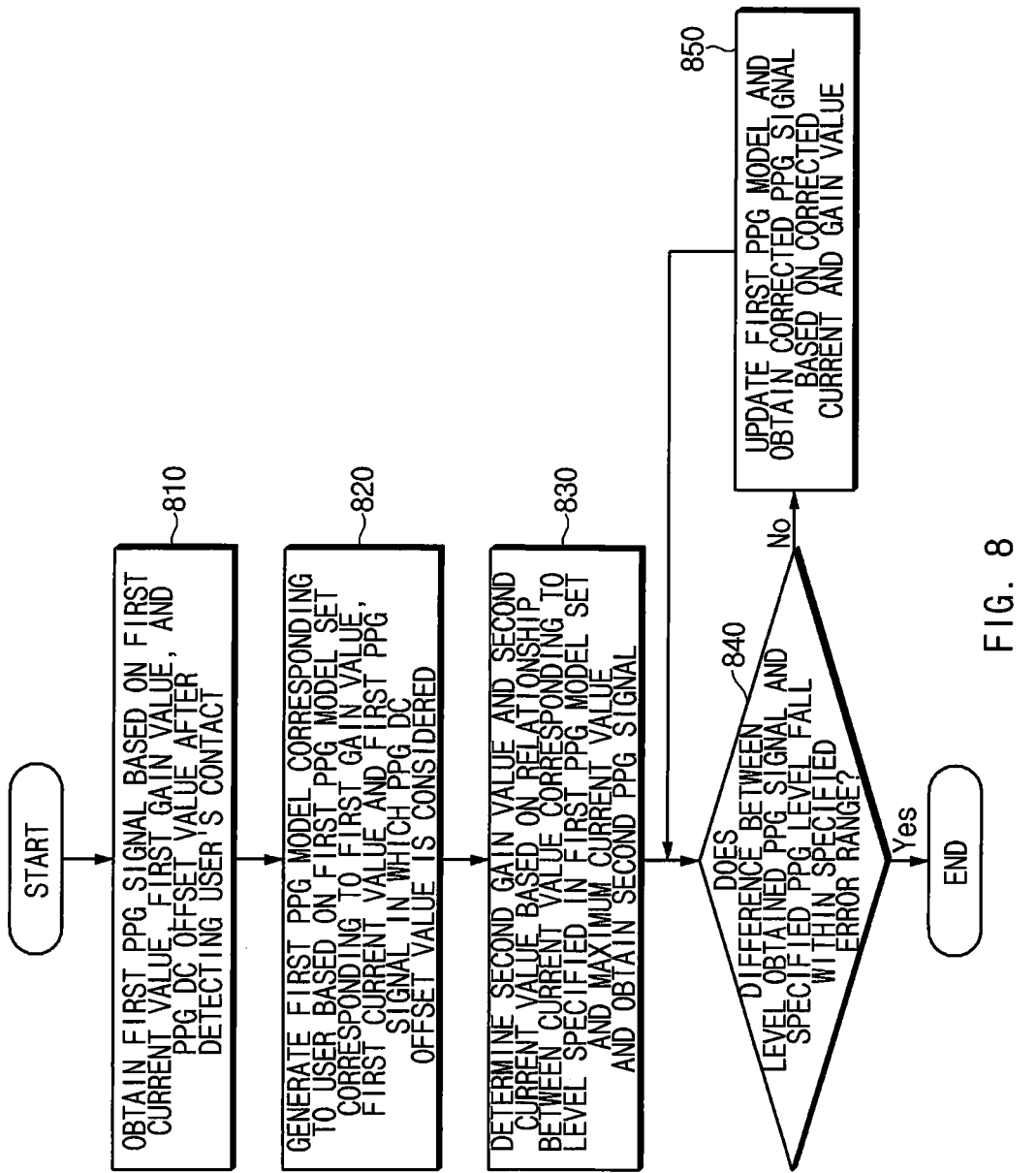
FIG. 8 is a flowchart of a method for correcting a PPG signal according to various embodiments.

FIG. 8 is a flowchart of a method for correcting a PPG signal according to various embodiments.

In operation 810, when the electronic device 100 detects that a user wears the electronic device, the electronic device 100 may acquire a PPG signal based on a current value, a gain value, and a PPG DC offset value set to initial values. For example, the electronic device 100 may acquire a first PPG signal based on the first current value, the first gain value, and the PPG DC offset value which are the initial values.

In various embodiments, the PPG DC offset value may have a value for acquiring a PPG signal having a level value in a range between the minimum value and the maximum value of the PPG level. The light detector 240 may subtract the set PPG DC offset value from a level of the acquired PPG signal. The PPG DC offset value may be preset in the light detector 240.

For example, it may be assumed that the level of the PPG signal measured based on the initial current value and the initial gain value is 200,000, and the maximum level of the PPG signal is 262,143. In this case, when the PPG DC offset value of the light detector 240 is set to 160,000, the level of the measured PPG signal may be 40,000. When the current value or gain value is increased two times to increase the SNR, the level of the PPG signal may be 80,000, which falls within the maximum level of the PPG signal. In a case in which the PPG DC offset value is 0, when the current value or the gain value is increased two times, the level of the PPG signal may be 400,000, resulting in saturation of the PPG signal.

In various embodiments, when the PPG DC offset value is not 0, the PPG level from which the PPG DC offset value is removed may be acquired. When the electronic device 100 is configured to have the PPG DC offset, the PPG DC offset value should be additionally considered in the above-described contents with reference to FIGS. 1 to 7B.

For example, when using the model interpolation scheme to generate the first PPG model 505 corresponding to the user in graph (1) of FIG. 5, when the PPG level value (Pa) for the initial current value (a) is measured, the model interpolation may be used based on (a, Pa+PPG DC offset value) rather than (a, Pa). The reason for this is that a plurality of PPG models by the statistical analysis presented in FIGS. 4 and 5 were created when the PPG DC offset value is 0.

As an additional example, in a case in which the first-order function is calculated by using two points (a, Pa) and (b, Pb) in FIG. 7B, when the PPG DC offset value is not 0, the first-order function may be calculated using (a, Pa+PPG DC offset value) and (b, Pb+PPG DC offset value), and it may be necessary to calculate the current value "t" corresponding to the Pt+PPG DC offset value, rather than the specified PPG level pt.

In operation 820, the electronic device 100 may generate a first PPG model corresponding to the user based on a first PPG model set corresponding to the first gain value, the first current value, and the first PPG signal considering the PPG DC offset value.

In operation 830, the electronic device 100 may determine a second gain value and a second current value based on a relationship between a current value corresponding to a level specified in the first PPG model set and a maximum current value, and acquire a second PPG signal.

In operation 840, the electronic device 100 may determine whether a difference between the level of the second PPG measured by the light detector 240 and the specified PPG level falls within a predetermined error range. When the difference falls within the predetermined error range, the electronic device 100 may finish the AGC operation.

When the difference is out of the predetermined error range, the electronic device 100 may update the first PPG model and acquire the PPG signal corrected based on the current value and gain value corrected according to the updated first PPG model in operation 850. The electronic device 100 may again determine whether the difference between the level of the PPG signal corrected and the specified PPG level falls within the predetermined error range in operation 840.

The electronic device 100 according to various embodiments may perform one or more correction operations to acquire a PPG signal having a specified level.

For example, in operation 850, the electronic device 100 may update the first PPG model based on the first data acquired in operation 810 and the second data obtained in operation 830. The first data may include the first current value, the first gain value, and the first PPG signal and the second data may include the second current value, the second gain value, and the second PPG signal. The electronic device 100 may update the first PPG model based on the relationship between the amount of increase/decrease in the current value and the gain value and the amount of increase/decrease in the level of the PPG signal. For example, the first-order function of the PPG level value according to the current value may be derived from the first data and the second data (the first-order function may be derived from two points on a graph). The first PPG model may be updated with the derived first-order function. The electronic device 100 may determine a third current value obtained by correcting the second current value and a third gain value obtained by correcting the second gain value based on the updated first PPG model, and acquire a third PPG signal. The third current value, the third gain value, and the third PPG signal may be referred to as third data.

The electronic device 100 may perform operation 840 on the third PPG signal. The electronic device 100 may again determine whether the difference between the level of the third PPG signal and the specified PPG level falls within the predetermined error range. When the difference falls within the predetermined error range, the electronic device 100 may finish the AGC operation. When the difference is out of a predetermined error range, the electronic device 100 may update the first PPG model based on the second data and the third data again. For example, the electronic device 100 may update the first model with a first-order function of a PPG level value according to a current value based on the second data and the third data.

The electronic device 100 may determine a fourth current value obtained by correcting the third current value and a fourth gain value obtained by correcting the third gain value based on the updated first model, and acquire a fourth PPG signal. The electronic device 100 may perform operation 840 again on the fourth PPG signal.

In various embodiments, the number of times of performance of AGC may vary according to a specified error range. For example, when the error range is specified to be within 5 to 10% of the maximum value of the PPG level, performance of AGC may be completed within one to three times of performance.

Figure 9:
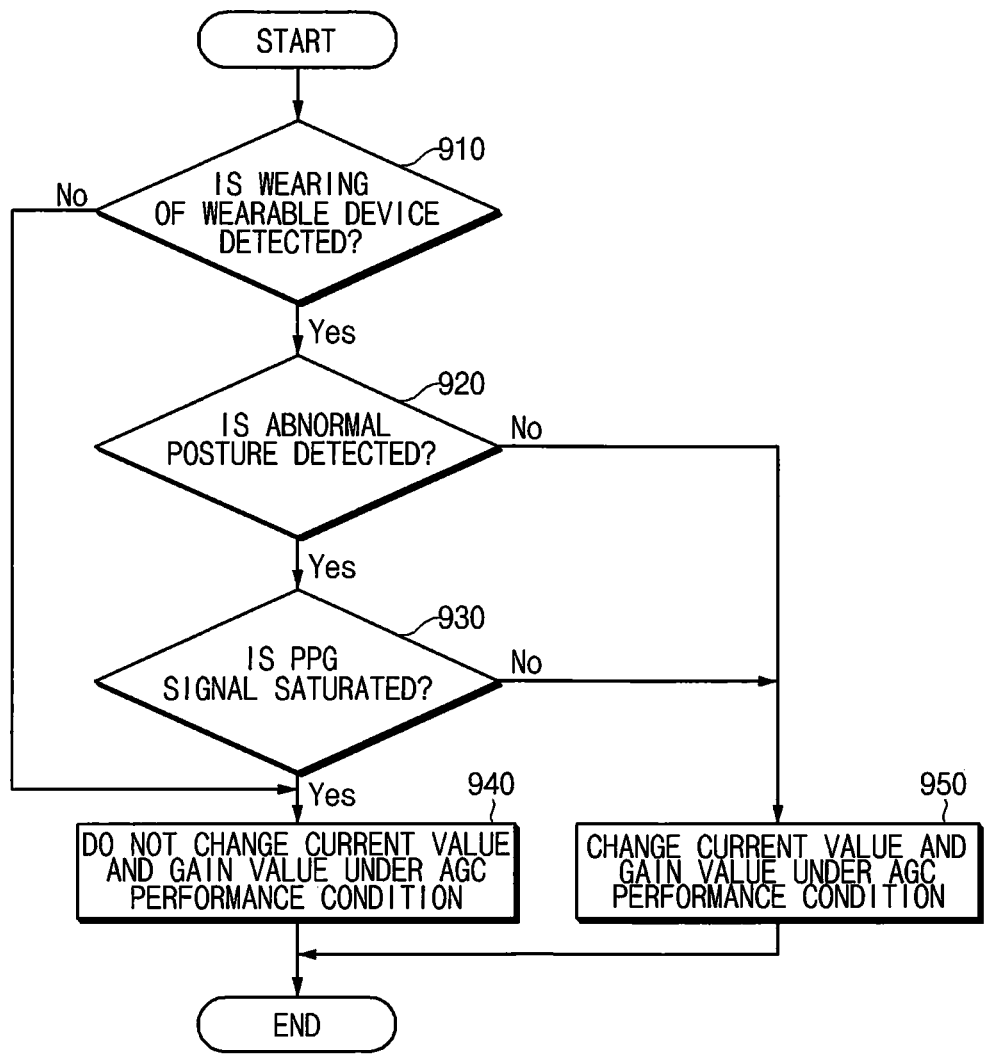
FIG. 9 is a flowchart of a method for determining whether to perform PPG measurement in consideration of a wearing posture of a wearable device according to various embodiments.

FIG. 9 is a flowchart of a method for determining whether to perform PPG measurement in consideration of a wearing posture of a wearable device according to various embodiments.

Referring to FIG. 9, a method for determining whether to perform PPG measurement in consideration of a wearing posture of a wearable device (e.g., the electronic device 100 of FIG. 2) according to various embodiments may include operations 910 to 950. The operations 910 to 950 may be performed, for example, by the electronic device 100 illustrated in FIG. 2. Each of the operations 910 to 950 may be implemented as instructions (commands) that may be performed (or executed) by the processor 110 of the electronic device 100, for example. The instructions may be stored in, for example, a computer recording medium or the memory 120 of the electronic device 100 shown in FIG. 2. Hereinafter, a description overlapping with the description with reference to FIG. 2 may be omitted.

In various embodiments, the electronic device 100 may be referred to as a wearable device. The electronic device 100 may not change a current value and a gain value although the AGC satisfies conditions for a change in the current value and the gain value in consideration of signal distortion even when the user's wearing is detected. For example, the PPG signal may be saturated depending on a wearing posture although the user wears the wearable device. For example, when the electronic device 100 worn on the user's wrist, such as a smart watch, is loosely worn, the PPG signal may be saturated although wearing is detected because the PPG sensor 200 touches the user's wrist.

In operation 910, the electronic device 100 may detect whether the user wears the electronic device 100. For example, the wearable device may detect whether the wearable device is worn using at least one of an infrared sensor (IR sensor) or the PPG sensor 200. When wearing is not detected, AGC may not be performed or PPG signal measurement may not be performed.

When it is detected that the electronic device 100 is worn, in operation 920, the electronic device 100 may determine whether a posture in which the electronic device 100 is worn is a predetermined abnormal posture. When an abnormal posture is not detected, the electronic device 100 may measure the PPG signal in operation 950.

When the electronic device 100 detects the abnormal posture, the electronic device 100 may determine whether the PPG signal is saturated in operation 930. When the PPG signal is saturated, the electronic device 100 may not change the current value or gain value although an AGC performance condition is satisfied in operation 940.

In various embodiments, the electronic device 100 may reduce the number of times of excessive performance of AGC by not performing the AGC operation in a situation in which the electronic device 100 is not worn or in a situation in which the electronic device 100 is worn in a posture that is not suitable for measuring a PPG signal.

In one embodiment, the electronic device 100 (e.g., the electronic device 100 of FIG. 2) may include an acceleration sensor. The electronic device 100 may estimate the posture of the electronic device 100 using an acceleration sensor. For example, when the user wears the electronic device 100 loosely on the user's wrist and poses with his arms down, the measured PPG signal may be saturated. The state in which the electronic device 100 is worn loosely on the wrist may be determined to be a case where the change in PPG is very large because the posture and operation state change within a short time. In this case, the electronic device 100 may not change the current value or the gain value even when the AGC performance condition is satisfied.

Figure 10:
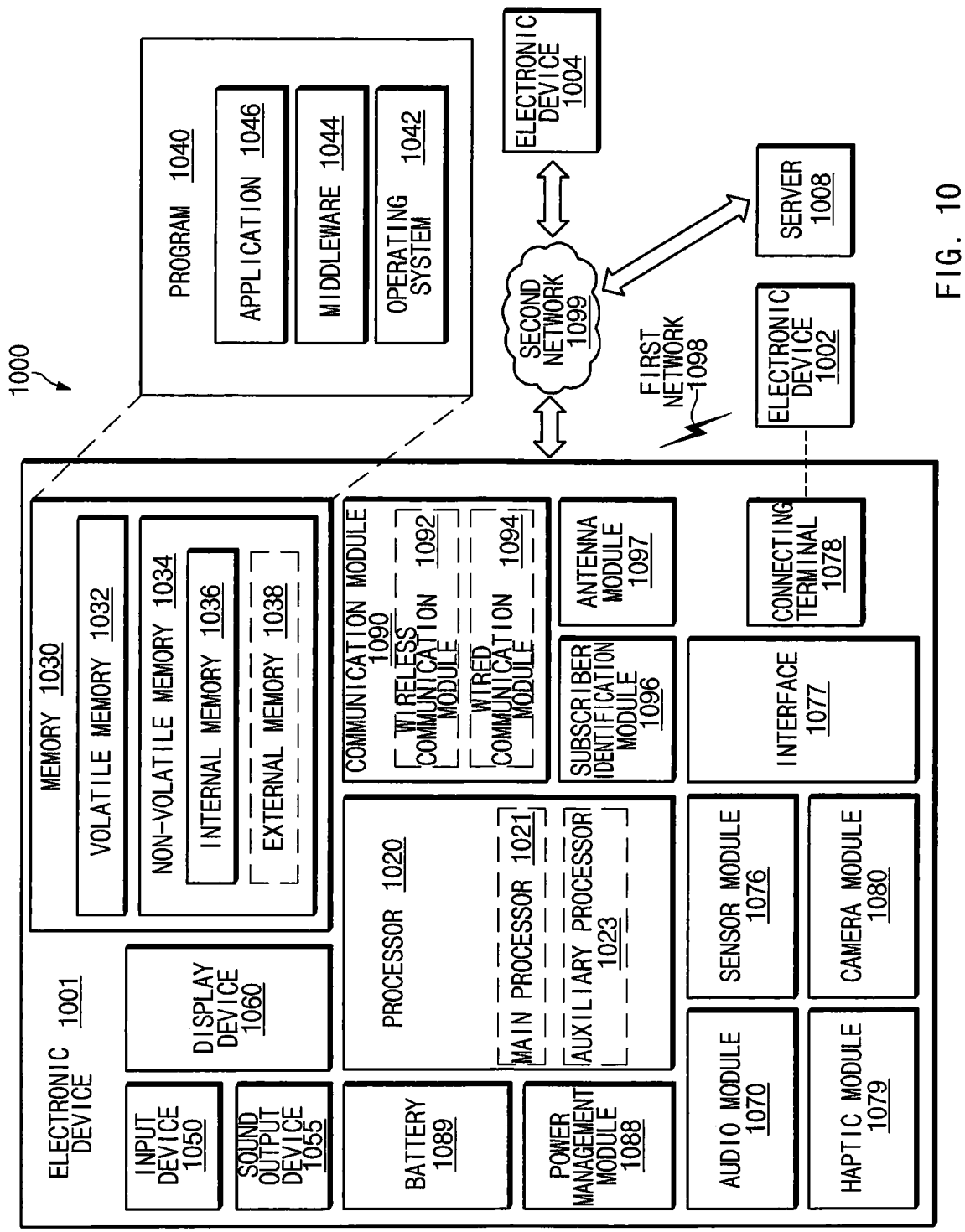
FIG. 10 is a block diagram of an electronic device in a network environment, according to various embodiments.

FIG. 10 is a block diagram illustrating an electronic device 1001 in a network environment 1000 according to various embodiments. Referring to FIG. 10, the electronic device 1001 in the network environment 1000 may communicate with an electronic device 1002 via a first network 1098 (e.g., a short-range wireless communication network), or an electronic device 1004 or a server 1008 via a second network 1099 (e.g., a long-range wireless communication network). According to an embodiment, the electronic device 1001 may communicate with the electronic device 1004 via the server 1008. According to an embodiment, the electronic device 1001 may include a processor 1020, memory 1030, an input device 1050, a sound output device 1055, a display device 1060, an audio module 1070, a sensor module 1076, an interface 1077, a haptic module 1079, a camera module 1080, a power management module 1088, a battery 1089, a communication module 1090, a subscriber identification module (SIM) 1096, or an antenna module 1097. In some embodiments, at least one (e.g., the display device 1060 or the camera module 1080) of the components may be omitted from the electronic device 1001, or one or more other components may be added in the electronic device 1001. In some embodiments, some of the components may be implemented as single integrated circuitry. For example, the sensor module 1076 (e.g., a fingerprint sensor, an iris sensor, or an illuminance sensor) may be implemented as embedded in the display device 1060 (e.g., a display).

The processor 1020 may execute, for example, software (e.g., a program 1040) to control at least one other component (e.g., a hardware or software component) of the electronic device 1001 coupled with the processor 1020, and may perform various data processing or computation. According to one embodiment, as at least part of the data processing or computation, the processor 1020 may load a command or data received from another component (e.g., the sensor module 1076 or the communication module 1090) in volatile memory 1032, process the command or the data stored in the volatile memory 1032, and store resulting data in non-volatile memory 1034. According to an embodiment, the processor 1020 may include a main processor 1021 (e.g., a central processing unit (CPU) or an application processor (AP)), and an auxiliary processor 1023 (e.g., a graphics processing unit (GPU), an image signal processor (ISP), a sensor hub processor, or a communication processor (CP)) that is operable independently from, or in conjunction with, the main processor 1021. Additionally or alternatively, the auxiliary processor 1023 may be adapted to consume less power than the main processor 1021, or to be specific to a specified function. The auxiliary processor 1023 may be implemented as separate from, or as part of the main processor 1021.

The auxiliary processor 1023 may control at least some of functions or states related to at least one component (e.g., the display device 1060, the sensor module 1076, or the communication module 1090) among the components of the electronic device 1001, instead of the main processor 1021 while the main processor 1021 is in an inactive (e.g., sleep) state, or together with the main processor 1021 while the main processor 1021 is in an active state (e.g., executing an application). According to an embodiment, the auxiliary processor 1023 (e.g., an image signal processor or a communication processor) may be implemented as part of another component (e.g., the camera module 1080 or the communication module 1090) functionally related to the auxiliary processor 1023.

The memory 1030 may store various data used by at least one component (e.g., the processor 1020 or the sensor module 1076) of the electronic device 1001. The various data may include, for example, software (e.g., the program 1040) and input data or output data for a command related thereto. The memory 1030 may include the volatile memory 1032 or the non-volatile memory 1034.

The program 1040 may be stored in the memory 1030 as software, and may include, for example, an operating system (OS) 1042, middleware 1044, or an application 1046.

The input device 1050 may receive a command or data to be used by other component (e.g., the processor 1020) of the electronic device 1001, from the outside (e.g., a user) of the electronic device 1001. The input device 1050 may include, for example, a microphone, a mouse, a keyboard, or a digital pen (e.g., a stylus pen).

The sound output device 1055 may output sound signals to the outside of the electronic device 1001. The sound output device 1055 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 1060 may visually provide information to the outside (e.g., a user) of the electronic device 1001. The display device 1060 may include, for example, a display, a hologram device, or a projector and control circuitry to control a corresponding one of the display, hologram device, and projector. According to an embodiment, the display device 1060 may include touch circuitry adapted to detect a touch, or sensor circuitry (e.g., a pressure sensor) adapted to measure the intensity of force incurred by the touch.

The audio module 1070 may convert a sound into an electrical signal and vice versa. According to an embodiment, the audio module 1070 may obtain the sound via the input device 1050, or output the sound via the sound output device 1055 or a headphone of an external electronic device (e.g., an electronic device 1002) directly (e.g., wiredly) or wirelessly coupled with the electronic device 1001.

The sensor module 1076 may detect an operational state (e.g., power or temperature) of the electronic device 1001 or an environmental state (e.g., a state of a user) external to the electronic device 1001, and then generate an electrical signal or data value corresponding to the detected state. According to an embodiment, the sensor module 1076 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 1077 may support one or more specified protocols to be used for the electronic device 1001 to be coupled with the external electronic device (e.g., the electronic device 1002) directly (e.g., wiredly) or wirelessly. According to an embodiment, the interface 1077 may include, for example, a high definition multimedia interface (HDMI), a universal serial bus (USB) interface, a secure digital (SD) card interface, or an audio interface.

A connecting terminal 1078 may include a connector via which the electronic device 1001 may be physically connected with the external electronic device (e.g., the electronic device 1002). According to an embodiment, the connecting terminal 1078 may include, for example, a HDMI connector, a USB connector, a SD card connector, or an audio connector (e.g., a headphone connector).

The haptic module 1079 may convert an electrical signal into a mechanical stimulus (e.g., a vibration or a movement) or electrical stimulus which may be recognized by a user via his tactile sensation or kinesthetic sensation. According to an embodiment, the haptic module 1079 may include, for example, a motor, a piezoelectric element, or an electric stimulator.

The camera module 1080 may capture a still image or moving images. According to an embodiment, the camera module 1080 may include one or more lenses, image sensors, image signal processors, or flashes.

The power management module 1088 may manage power supplied to the electronic device 1001. According to one embodiment, the power management module 1088 may be implemented as at least part of, for example, a power management integrated circuit (PMIC).

The battery 1089 may supply power to at least one component of the electronic device 1001. According to an embodiment, the battery 1089 may include, for example, a primary cell which is not rechargeable, a secondary cell which is rechargeable, or a fuel cell.

The communication module 1090 may support establishing a direct (e.g., wired) communication channel or a wireless communication channel between the electronic device 1001 and the external electronic device (e.g., the electronic device 1002, the electronic device 1004, or the server 1008) and performing communication via the established communication channel. The communication module 1090 may include one or more communication processors that are operable independently from the processor 1020 (e.g., the application processor (AP)) and supports a direct (e.g., wired) communication or a wireless communication. According to an embodiment, the communication module 1090 may include a wireless communication module 1092 (e.g., a cellular communication module, a short-range wireless communication module, or a global navigation satellite system (GNSS) communication module) or a wired communication module 1094 (e.g., a local area network (LAN) communication module or a power line communication (PLC) module). A corresponding one of these communication modules may communicate with the external electronic device via the first network 1098 (e.g., a short-range communication network, such as Bluetooth™, wireless-fidelity (Wi-Fi) direct, or infrared data association (IrDA)) or the second network 1099 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 1092 may identify and authenticate the electronic device 1001 in a communication network, such as the first network 1098 or the second network 1099, using subscriber information (e.g., international mobile subscriber identity (IMSI)) stored in the subscriber identification module 1096.

The antenna module 1097 may transmit or receive a signal or power to or from the outside (e.g., the external electronic device) of the electronic device 1001. According to an embodiment, the antenna module 1097 may include an antenna including a radiating element composed of a conductive material or a conductive pattern formed in or on a substrate (e.g., PCB). According to an embodiment, the antenna module 1097 may include a plurality of antennas. In such a case, at least one antenna appropriate for a communication scheme used in the communication network, such as the first network 1098 or the second network 1099, may be selected, for example, by the communication module 1090 (e.g., the wireless communication module 1092) from the plurality of antennas. The signal or the power may then be transmitted or received between the communication module 1090, and the external electronic device via the selected at least one antenna. According to an embodiment, another component (e.g., a radio frequency integrated circuit (RFIC)) other than the radiating element may be additionally formed as part of the antenna module 1097.

At least some of the above-described components may be coupled mutually and communicate signals (e.g., commands or data) therebetween via an inter-peripheral communication scheme (e.g., a bus, general purpose input and output (GPM), serial peripheral interface (SPI), or mobile industry processor interface (MIPI)).

According to an embodiment, commands or data may be transmitted or received between the electronic device 1001 and the external electronic device 1004 via the server 1008 coupled with the second network 1099. Each of the electronic devices 1002 and 1004 may be a device of a same type as, or a different type, from the electronic device 1001. According to an embodiment, all or some of operations to be executed at the electronic device 1001 may be executed at one or more of the external electronic devices 1002, 1004, or 1008. For example, if the electronic device 1001 should perform a function or a service automatically, or in response to a request from a user or another device, the electronic device 1001, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 1001. The electronic device 1001 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smartphone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include any one of, or all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 1040) including one or more instructions that are stored in a storage medium (e.g., internal memory 1036 or external memory 1038) that is readable by a machine (e.g., the electronic device 1001). For example, a processor (e.g., the processor 1020) of the machine (e.g., the electronic device 1001) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., PlayStore™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

The invention claimed is:

1. An electronic device comprising:
   a photoplethysmography (PPG) sensor including a light emitter configured to apply a current in a specified range and emit a light signal corresponding to the current and a light detector configured to amplify a received light signal by applying one of a plurality of gain values;
   a memory configured to store a plurality of sets of PPG models corresponding to the plurality of gain values and including a current value and PPG level data corresponding to the current value, wherein each PPG model corresponds to a first-order function with a current value applied to the light emitter on an x-axis and a level value of a PPG signal acquired by the PPG sensor on a y-axis; and
   at least one processor electrically connected to the PPG sensor and the memory,
   wherein the at least one processor is configured to:
   acquire a first PPG signal from the PPG sensor with a first current value satisfying the specified range and a first gain value of the plurality of gain values when a contact of a user is detected by the PPG sensor,
   select two PPG models from the plurality of sets of PPG models located closest from a point where a value of the x-axis is the first current value and a value of the y-axis is a level value of the first PPG signal,
   generate a customized PPG model corresponding to the user based on the two PPG models,
   determine a second gain value and a second current value for acquiring a PPG signal with a specified PPG level based at least on the customized PPG model, and
   obtain a second PPG signal with the specified PPG level using the PPG sensor with the second gain value and the second current value.

2. The electronic device of claim 1, wherein the at least one processor is configured to generate bio information for the user based at least on the second PPG signal.

3. The electronic device of claim 1, wherein the at least one processor is configured to:
   identify a current value for acquiring the second PPG signal with the specified PPG level based at least on the customized PPG model, when the current value satisfies the specified range, and
   determine the second gain value to be the first gain value and determine the second current value to be the first current value.

4. The electronic device of claim 1, wherein the at least one processor is configured to:
   identify a current value for acquiring the second PPG signal with the specified PPG level based at least on the customized PPG model, when the current value does not satisfy the specified range, and
   determine the second gain value to be a third gain value greater or less than the first gain value and determine the second current value to be a third current value corresponding to the third gain value and satisfying the specified range.

5. The electronic device of claim 1, wherein the at least one processor is configured to:
   determine a third current value obtained by correcting the second current value using the first current value, the first PPG signal, the second current value and the second PPG signal, and
   obtain a third PPG signal satisfying the specified PPG level using the PPG sensor set with the second gain value and the third current value.

6. The electronic device of claim 5, wherein the at least one processor is configured to:
   update the customized PPG model using the first current value, the first PPG signal, the second current value and the second PPG signal, and
   determine the third current value based on the updated customized PPG model.

7. The electronic device of claim 5, wherein the at least one processor is configured to:
   determine the second gain value to be a fourth gain value greater than the second gain value and determine a fourth current value corresponding to the fourth gain value and satisfying the specified range when the third current value does not satisfy the specified range, and
   obtain the third PPG signal from the PPG sensor with the third gain value and the fourth current value.

8. The electronic device of claim 1, further comprising:
   an acceleration sensor,
   wherein the at least one processor is configured to determine whether to perform an operation of acquiring the first PPG signal using the PPG sensor based at least on movement information acquired using the acceleration sensor.

9. The electronic device of claim 8, wherein the at least one processor is configured to:
   obtain temporary PPG signals based on the first current value and the first gain value after the contact of the user is detected,
   obtain acceleration values of the electronic device from the acceleration sensor, and
   obtain the first PPG signal when a change width in the acceleration values is less than a predetermined threshold value and a change width in the temporary PPG signals is less than a predetermined threshold value.

10. A method performed by an electronic device, comprising:
    obtaining a first PPG signal from a photoplethysmography (PPG) sensor using a first current value less than or equal to a maximum current value applicable to the PPG sensor and a first gain value of a plurality of gain values in the PPG sensor when a contact of a user is detected by the PPG sensor included in the electronic device;
    selecting two PPG models from a plurality of sets of PPG models corresponding to the first gain value based at least on the first current value and the first PPG signal, wherein each PPG model corresponds to a first-order function with a current value applied to the light emitter on an x-axis and a level value of a PPG signal acquired by the PPG sensor on a y-axis, wherein the two PPG models are closest from a point where a value of the x-axis is the first current value and a value of the y-axis is a level value of the first PPG signal;
    generating a customized PPG model corresponding to the user based on the two PPG models; and
    obtaining a second PPG signal having a specified PPG level from the PPG sensor using a second gain value and a second current value determined based on a relationship between a current value corresponding to the specified PPG level based on the customized PPG model and the maximum current value applicable to the PPG sensor.

11. The method of claim 10, further comprising:
determining a third current value obtained by correcting the second current value using the first current value, the first PPG signal, the second current value and the second PPG signal; and
obtaining a third PPG signal having the specified PPG level from the PPG sensor using the second gain value and the third current value.

12. The method of claim 11, further comprising:
determining a third gain value that is a value greater than the second gain value and determine a fourth current value less than the maximum current value applicable to the PPG sensor and corresponding to the third gain value when the third current value is greater than the maximum current value applicable to the PPG sensor; and
obtaining the third PPG signal from the PPG sensor with the third gain value and the fourth current value.

* * * * *